US008263564B2

(12) United States Patent
Reim et al.

(10) Patent No.: US 8,263,564 B2
(45) Date of Patent: Sep. 11, 2012

(54) IRON-CARBOHYDRATE COMPLEX COMPOUNDS

(75) Inventors: Stefan Reim, St. Gallen (CH); Peter Geisser, St. Gallen (CH)

(73) Assignee: Vifor (International) AG, St. Gallen (CH)

(*) Notice: Subject to any disclaimer, the term of this patent is extended or adjusted under 35 U.S.C. 154(b) by 421 days.

(21) Appl. No.: 12/523,331

(22) PCT Filed: Jan. 15, 2008

(86) PCT No.: PCT/EP2008/050387
§ 371 (c)(1),
(2), (4) Date: Aug. 13, 2009

(87) PCT Pub. No.: WO2008/087135
PCT Pub. Date: Jul. 24, 2008

(65) Prior Publication Data
US 2010/0035830 A1 Feb. 11, 2010

(30) Foreign Application Priority Data
Jan. 19, 2007 (EP) .................................. 07100803

(51) Int. Cl.
*A01N 43/04* (2006.01)
*A61K 31/70* (2006.01)

(52) U.S. Cl. ............... 514/23; 514/53; 514/54; 514/60; 514/61; 536/1.11; 536/102; 536/114; 536/121

(58) Field of Classification Search ........................ None
See application file for complete search history.

(56) References Cited

U.S. PATENT DOCUMENTS

| 4,599,405 A * | 7/1986 | Muller et al. ................. 536/113 |
| 6,461,651 B1 | 10/2002 | Leusner et al. |
| 2006/0205691 A1 | 9/2006 | Geisser et al. |

FOREIGN PATENT DOCUMENTS

| EP | 0044050 A2 | 1/1982 |
| GB | 1111929 | 5/1968 |
| RU | 2198665 | 2/2003 |
| WO | 2005/000210 A2 | 1/2005 |
| WO | 2005/116046 A1 | 12/2005 |

OTHER PUBLICATIONS

"Derivative", Merriam-Webster's Online Dictionary < http://www.merriam-webstercom/dictionary/derivative >, accessed Jan. 6, 2012.*
Rao et al. Inorganica Chimica Acta (2000), vol. 297, pp. 373-382.*
International Search Report for corresponding PCT/EP2008/050387 mailed Jun. 30, 2008, three pages.
International Preliminary Report on Patentability for corresponding PCT/EP2008/050387 mailed Aug. 13, 2009, ten pages.
Hentze et al., "Balancing Acts: Molecular Control of Mammalian Iron Metabolism," Cell, vol. 117, pp. 285-297, Apr. 30, 2004.
Berenbaum et al., "Animal and Human Studies on Ferrous Fumarate," from www.bloodjournal.org on Jul. 7, 2008, four pages.
Berenbaum et al., "Animal and Human Studies on Ferrous Fumarate, an Oral Hematinic," from www.bloodjournal.org on Jul. 7, 2008, seven pages.

* cited by examiner

*Primary Examiner* — Patrick Lewis
(74) *Attorney, Agent, or Firm* — Rankin, Hill & Clark LLP

(57) ABSTRACT

The invention provides an iron-carbohydrate complex compound which is characterized by a content of iron(II). The invention also provides processes for the preparation of the iron-carbohydrate complex compound and the use thereof for treatment of iron deficiency anaemias.

23 Claims, No Drawings

IRON-CARBOHYDRATE COMPLEX COMPOUNDS

The invention relates to iron-carbohydrate complex compounds which contain iron(II) in addition to iron(III), processes for their preparation, medicaments containing them and the use thereof for treatment of iron deficiency anaemias.

According to the prior art, anaemias caused by iron deficiency are treated by therapy or prophylactically in particular by parenteral administration of medicaments containing iron (III), and in particular by oral administration of medicaments containing iron(II) or iron(III). Parenteral administration of iron (II) therefore does not take place.

A preparation frequently used in practice is a water-soluble iron(III) hydroxide-sucrose complex (Danielson, Salomonson, Derendorf, Geisser, Drug Res., vol. 46: 615-621, 1996), which is particularly suitable for parenteral administration.

WO2004/037865 A1 discloses a water-soluble iron(III) hydroxide-carbohydrate complex which can be used predominantly parenterally, but also orally. It is a complex of iron(III) with maltodextrins having a dextrose equivalent of from 5 to 20, the molecular weight of the complex being 80 to 400 kDa.

A further successfully used preparation which can be administered orally is based on an iron(III) hydroxide-polymaltose complex having a molecular weight of about 50 kDa, which is commercially obtainable as Maltofer®.

Oral iron(II) preparations which are available on the market are, in particular, iron(II) fumarate, sulfate and glycollate.

Clinical studies have shown that iron(II) compounds in general are absorbed more rapidly. There are theories according to which iron(III) is absorbed via a divalent intermediate stated on oral intake [Hentze, M. W., Muckenthaler, M. U. and Andrews N. C. (2004) Balancing acts: Molecular Control of Mammalian Iron Metabolism, Cell, 117, 285-297]. However, iron(II) cannot be administered parenterally because of the high toxicity. It leads to increased side effects on oral administration. Oral administration of iron(II) is therefore not preferred.

The invention was therefore based on the object of providing an improved medicament by means of which iron is absorbed particularly well by the body especially on oral administration. In particular, the iron should be absorbed as swiftly as possible and should have a better tolerability than pure iron(II) preparations.

The object is achieved according to the invention by providing an iron-carbohydrate complex compound which has a high content of iron(II) with a tolerably low toxicity.

The invention thus provides an iron-carbohydrate complex compound, which is characterized in that its content of iron (II), based on the total amount of iron in the complex compound, is at least 2 wt. %.

The iron-carbohydrate complex compounds according to the invention are, in particular, oligo- or polynuclear iron compounds in which the iron atoms are bonded to one another in particular via oxygen atoms and/or hydroxyl groups, and wherein the carbohydrates are present partly bonded as a complex and/or via hydrogen bridge bonds. Furthermore, oxidized carbohydrate molecules can be present bonded as a complex via carboxylate groups, as described below. The iron-carbohydrate complex compounds can furthermore also contain water bonded as a complex or via hydrogen bridge bonds.

The iron-carbohydrate complex compounds according to the invention are characterized by their content of iron(II). This means that in the iron-carbohydrate complex compound according to the invention, some of the iron is present in the oxidation level of 2+. The remaining iron is present in the iron-carbohydrate complex compound according to the invention practically exclusively in the oxidation level of 3+, i.e. as iron(III). These are therefore so-called "mixed valence" compounds, in which the metal is present in several oxidation levels side by side.

According to the invention, the content of iron(II) in the total iron content is at least 2 wt. %, preferably more than 3 wt. %, based on the total amount of iron in the iron-carbohydrate complex compound. Preferably, the content of iron(II) in the total iron content is 3 to 50 wt. %, more preferably 5 to 40 wt. %, particularly preferably 7 to 35 wt. %, in each case based on the total amount of iron in the iron-carbohydrate complex compound. The iron(II) content can be determined, in particular, by a titrimetric determination (see, for example: Jander Jahr, Maβanalyse [Volumetric Analysis] 15th edition, Verlag Walter de Gruyter, 1989). In this analysis, the total iron is first determined using $H_2O_2$, and then iron(III) without the use of $H_2O_2$, and the content of iron(II) is determined by obtaining the difference.

The content of total iron in the weight of the iron-carbohydrate complex compound is preferably 5 to 40 wt. %, preferably 10 to 30 wt. %.

In a preferred embodiment, the content of carbohydrate (or carbohydrates) in the weight of the complex compound is 10 to 80 wt. %, preferably 20 to 70 wt. %, particularly preferably 35 to 65 wt. %.

The amounts data based, in the context of the present invention, on the weight of the iron-carbohydrate complex compound always relate to the total weight of the iron-carbohydrate complex compound according to the invention, including, for example, the water content which may result from the preparation, as described below.

In addition to iron(III), iron(II) and one or more carbohydrates, the iron-carbohydrate complex compound-according to the invention contains hydroxyl groups (in general designated $OH^-$), oxo groups (in general designated $O^{2-}$), optionally further anions and water. The ionogenic style of writing as $OH^-$ or $O^{2-}$ in this context does not of course rule out that these groups can have more or less covalent bonding contents in their bonding to iron cations. This is well-known to the person skilled in the art.

In addition to the carbohydrates, the iron-carbohydrate complex compounds according to the invention can also contain other ligands, for example carboxylic acids, such as gluconic acid, lactic acid etc.

The content of water in the iron-carbohydrate complex compound according to the invention in this context can expediently be up to 10 wt. %, depending on the drying conditions. Preferably, the water content is 2 to 8 wt. %.

An iron-carbohydrate complex compound according to the invention has, for example, the following composition:
  5 to 40 wt. % of iron, of which preferably 3 to 50 wt. %, more preferably 5 to 40 wt. %, based on the total amount of iron, is present in the form of iron(II),
  10 to 80 wt. %, preferably 20 to 70 wt. %, particularly preferably 35 to 65 wt. % of one or more carbohydrates,
  remainder: oxygen and hydrogen in bonded form (apart from in the carbohydrate) and optionally further elements.

As stated above, the elements oxygen and hydrogen are present in particular as hydroxyl groups, oxo groups and optionally water. Further elements, in addition to iron, carbon, oxygen, hydrogen and nitrogen, can result, for example, from introduction from the iron(III) salt used during the preparation and, where appropriate, acids and/or bases used during the preparation. They are thus, for example, chlorine (for example from Cl$^-$), sulfur, for example from sulfate (SO$_4^{2-}$), nitrogen, for example from nitrate (NO$_3^-$) and alkali metals and alkaline earth metals from the bases used, such as alkali metal and alkaline earth metal hydroxides, carbonates or bicarbonates etc. The content of further elements is in general less than 15, more preferably less than 10 wt. %, based on the weight of the iron-carbohydrate complex compound according to the invention.

The following composition is preferred:
  10 to 30 wt. % of iron, of which preferably 5 to 40 wt. %, based on the total amount of iron, is present in the form of iron(II),
  20 to 70 wt. % of one or more carbohydrates,
  remainder: oxygen and hydrogen in bonded form (apart from in the carbohydrates) and optionally further elements, as explained above.

In a particular embodiment of the invention, the weight-average molecular weight of the iron-carbohydrate complex compound according to the invention is 10 to 80 kDa, preferably 12 to 65 kDa, particularly preferably 15 to 60 kDa. The weight-average molecular weight is determined in this context by gel permeation chromatography against pullulan as the standard (for example as described by Geisser et al. in Arzneim. Forsch./Drug Res. 42 (II), 12, 1439-1452 (1992), paragraph 2.2.5).

The iron-carbohydrate complex compound according to the invention contains one or more carbohydrates which are present, for example, in the compounds according to the invention bonded as a complex and/or via hydrogen bridge bonds to iron or iron-containing partial structures. The iron-carbohydrate complex compound contains at least one carbohydrate, for example chosen from natural carbohydrates or synthetic carbohydrate derivatives, such as starch, hydrolyzed starches, such as dextrins (in particular maltodextrin, maltose syrup, glucose syrup), cyclodextrins, dextrans, saccharides.

According to the invention, the term carbohydrates or carbohydrate ligands includes all natural carbohydrates, all synthetic or semi-synthetic carbohydrate derivatives and saccharides.

According to the invention, the term carbohydrates furthermore also includes the carbohydrate ligands which are formed from the preparation process, which is preferred according to the invention, of the reaction of iron(III) salts with carbohydrates with oxidation of the carbohydrates and reduction of the iron(III) to form iron(II) in the sense of a redox reaction. In this redox reaction, an oxidation of the aldehyde and/or keto groups (after rearrangement in an alkaline medium) of the carbohydrates in general takes place to give carboxyl groups, on which, for example, the known detection methods for carbohydrates are also based. The oxidized carbohydrate-ligand molecules which form in situ to a certain extent in this context and contain carboxyl groups are of course also contained in the scope of the invention. The carboxyl groups can be present bonded via hydrogen bridge bonds or anionic carboxylate groups to iron or iron-containing partial structures, in general directly to iron.

The oxidized carbohydrate molecules thus in particular also contain carboxyl groups, which also lead to firmer bonding of the carbohydrate ligands to the iron.

It can furthermore be seen from the above that the carbohydrates employed according to the invention during the preparation of the iron-carbohydrate complex compound are preferably those which have the ability to reduce iron(III) to iron(II).

Carbohydrates or carbohydrate derivatives which are preferably employed according to the invention include dextrins, such as, in particular, maltodextrin and maltose syrup, as well as glucose syrups.

Carbohydrates and derivatives thereof are described, for example, in Römpp-Lexikon, Biotechnologie und Gentechnik [Römpp's Dictionary, Biotechnology and Genetic Engineering], Georg Thieme Verlag 1999, and in Lehrbuch der Lebensmittelchemie [Textbook of Food Chemistry], H. -D. Belitz and W. Grosch, 4th edition, Springer-Verlag.

They include, as the person skilled in the art knows, in particular the natural substance class of polyhydroxycarbonyl compounds and oligo- and polycondensates thereof. Non-condensed representatives, such as the monosaccharides, have carbon chains having at least three C atoms and at least one chirality centre. The invention includes all the isomers, such as structural isomers, enantiomers or diastereomers, of the carbohydrates mentioned according to the invention and their derivatives. The most widespread are monosaccharides having five or six C atoms. Di- and multi-sugars are mono-sugars linked in chains via glycosidic bonds. The monosaccharides (mono-sugars) include e.g. glucose and fructose. The disaccharides include e.g. crystal sugar, lactose and maltose. The oligosaccharides include, for example, raffinose. The polysaccharides include, in particular, starch and derivatives thereof and dextrans (exopolysaccharides from bacteria). Starch derivatives, such as dextrins, are particularly preferred according to the invention. The term dextrins according to Römpp-Lexikon, Biotechnologie und Gentechnik [Römpp's Dictionary, Biotechnology and Genetic Engineering] (ibid.) is a collective name for various lower and higher polymers of D-glucose units of the general, formula $(C_6H_{10}O_5)_n.H_2O$ which are formed by incomplete hydrolysis of starch, e.g. with dilute acids, by the action of heat or by the action of enzymes. A carbohydrate which is preferred according to the invention is a preferably incompletely hydrolyzed starch which has a DE value of between 0 and 100. According to the invention, it includes dextrins, such as maltodextrins and maltose syrups, as well as glucose syrups. The maltodextrins which are particularly preferred according to the invention are preferably prepared by enzymatic cleavage of maize starch or potato starch with alpha-amylase. The degree of hydrolysis is conventionally stated in these products by the so-called DE value (dextrose equivalent). For this purpose, the increase in the ability of a starch solution to effect reduction as hydrolysis progresses is determined. Native starch has the value DE=0, after complete hydrolysis to glucose the theoretical DE value is 100, and a complete cleavage to maltose leads to a DE value of 52.6. The hydrolyzed starches maltodextrin and maltose syrup which are preferred according to the invention expediently have a DE value of from about 3 to 50. In this context, the transition between maltodextrins and maltose syrups is as a rule smooth. As a result of their lower degree of hydrolysis, maltodextrins of course have lower DE values than maltose syrups. Glucose syrups in general have higher DE values than maltose syrups (in particular also more than 50), here also to this extent the transition between maltose syrups and glucose syrups as a rule being smooth. In the context of the present invention, glucose syrups in general are said to have DE values of more than 50.

According to the invention, the maltodextrins and maltose syrups preferably used preferably have DE values of from 5 to 45, particularly preferably from 7 to 40.

According to the invention, the dextrose equivalents are determined, in particular, gravimetrically. For this, the carbohydrates are reacted in aqueous solution with Fehling's solution while boiling. The reaction takes place quantitatively, i.e.

until no further decolouration of the Fehling's solution occurs. The copper(I) oxide which has precipitated out is dried to constant weight at 105° C. and determined gravimetrically. From the values obtained, the glucose content (dextrose equivalent) is calculated as % wt./wt. of the dextrin dry substance. The following solutions, for example, can be used: 25 ml of Fehling's solution I, mixed with 25 ml of Fehling's solution II; 10 ml of aqueous carbohydrate solution (10% mol/vol.) (Fehling's solution I: 34.6 g of copper(II) sulfate dissolved in 500 ml of water; Fehling's solution II: 173 g of potassium sodium tartrate and 50 g of sodium hydroxide dissolved in 400 ml of water).

It is also possible to determine the DE values titrimetrically by the method of Lane and Eynon (ISO 5377-1981 (E)), which leads to comparable results in a first approximation.

The number-average molecular weight of the carbohydrates preferably used is expediently up to about 50,000.

The invention also provides a preferred process for the preparation of an iron-carbohydrate complex compound, which comprises the steps:
a) preparation of an aqueous solution or suspension of a carbohydrate,
b) addition of an iron(III) salt, preferably at a constant pH in the range of 7-13,
c) heating of the aqueous solution or suspension,
d) cooling of the aqueous solution or suspension and
e) isolation of the iron-carbohydrate complex compound formed.

According to the invention, iron(II) salts or mixtures of iron(II) and iron(III) salts can also be employed in step b). In this context, the use of reducing carbohydrates can be omitted. According to the invention, it is furthermore possible also to add during the preparation of the iron-carbohydrate complex compounds additional reducing agents, such as e.g. vitamin C, dihydroflavones or hyperoxides, which effect a reduction of the iron (III) to iron (II).

In a preferred embodiment of the process according to the invention, after cooling of the aqueous solution or suspension in step d), step d') of adjusting the pH of the aqueous solution or suspension to a physiologically acceptable value of preferably about 5 to 9 is carried out.

Solids which may be formed during the reaction are separated off in particular after step d'), after which the iron complex can be precipitated out and isolated.

The addition of the iron(III) salt (or of the iron(II) salt or of a mixture of iron(III) and iron(II) salts) in step b) is carried out, for example, by dropwise addition of a solution or suspension, while stirring. Iron(III) salts (or iron(II) salts) which can preferably be used are water-soluble salts of inorganic or organic acids or mixtures thereof, such as halides, e.g. chlorides, or sulfates. Iron hydroxides can also be employed under appropriate conditions. Physiologically acceptable salts are preferably used. An aqueous solution of iron(III) chloride is particularly preferably used, preferably together with a carbohydrate having reducing properties. Fe(III) sulfate solutions and mixtures of iron(III) salt solutions can also be used.

The addition of the iron(III) salt (or of the iron(II) salt or of a mixture of iron(III) and iron(II) salts) is expediently carried out according to the invention at pH values of from 7 to 13, preferably at a pH of from 9 to 12. In order to achieve these pH values and to keep them constant in the course of the reaction, bases are expediently added, such as, in particular, alkali metal or alkaline earth metal hydroxides, such as sodium, potassium, calcium and magnesium hydroxide, particularly preferably sodium hydroxide, or also alkali metal or alkaline earth metal carbonates or bicarbonates. For example, the process can be carried out such that an aqueous carbohydrate solution is heated to the desired temperature of, for example, 50 to 70° C. and the base and iron(III) salt solution are added dropwise such that the pH is kept constant (for example with a deviation of a maximum of one, preferably 0.5 pH units), and optionally also the temperature is kept substantially constant. At this pH, the iron(III) salt (or the iron(II) salt or a mixture of iron(III) and iron(II) salt) reacts substantially to form iron(III)- (or iron(II))-hydroxide bonds. At the same time, complexing with the carbohydrate also already takes place.

When the addition of the iron(III) salt solution (or of the iron(II) salt solution or of a mixture of iron(III) and iron(II) salt solutions) and of the base solution has ended, the solution or suspension obtained is heated up. A further reaction takes place, in which some of the iron(III) is preferably reduced to iron(II) by aldehyde groups contained in the carbohydrate employed. In this context, heating of the solution is preferably carried out to temperatures above 80° C., preferably above 90° C., particularly preferably at the boiling point of water (100° under normal pressure). The heat treatment of step c) is expediently carried out for at least 30 min. The heat treatment in general does not last longer than 5 h. The solution is then cooled, preferably to 0° C. to 30 ° C., in particular 25° C. (room temperature).

When the reaction has taken place, the solution or suspension obtained is cooled and optionally diluted. After the cooling, the pH is preferably adjusted to a physiologically acceptable value of between 5 and 9, preferably 5.5 and 8.5. Acids which can be employed are inorganic or organic acids or mixtures thereof, in particular hydrogen halide acids, such as hydrogen chloride or aqueous hydrochloric acid, or sulfuric acid. Solids and impurities possibly present can then be separated off, for example by filtration or centrifugation.

Under the abovementioned conditions, the iron-carbohydrate complex compound according to the invention with its content of at least 2 wt. % of iron(II), based on the amount of iron, can be obtained.

The iron-carbohydrate complex compounds according to the invention are in general readily soluble in water. According to the invention, this means that preferably more than 30 g, more preferably more than 35 g, particularly preferably more than 40 g of the iron-carbohydrate complex compound according to the invention dissolve in 100 g of water at 25°. The maximum solubility is, for example, about 100 g to 120 g, in each case per 100 g of water at 25° C.

The solutions of the iron-carbohydrate complex, compounds preferably obtained according to the invention can be used directly for the preparation of medicaments. For this, the solutions are purified by reverse osmosis or dialysis. The purification can serve in particular to remove salts. However, it is also possible first to isolate the iron(III)(II)-carbohydrate complex compounds from the solution, for example by precipitation with an alcohol, such as an alkanol, for example ethanol or propanol. The iron complex according to the invention obtained in this way can additionally be after-treated for further purification, for example by mixing it with ethanol, filtering the mixture and vacuum drying the solid. The isolation can also be carried out by spray drying after reverse osmosis or dialysis of the solution containing the iron-carbohydrate complex compound.

The invention also provides a medicament containing an iron-carbohydrate complex compound according to the invention. Sterile aqueous solutions in particular can be prepared from the iron-carbohydrate complex compound according to the invention.

The solutions according to the invention are suitable in particular for oral administration, but they can also be employed parenterally for injections or infusions, for example intravenously or intramuscularly.

Solutions which can be administered parenterally can be prepared in a conventional manner, optionally co-using conventional additives for parenteral solutions. The solutions can be formulated such that they can be administered as such by injection or as an infusion, e.g. in saline solution.

For oral administration, the complexes according to the invention can be pressed to tablets or filled into capsules in the conventional manner with conventional excipients.

Preparations which are stable over a relatively long period of time, such as tablets (chewing, film-coated, effervescent tablets), effervescent granules, powder mixtures, sachets, and in which the iron(III)(II) complex is present are, for example, also suitable.

Solid unit dosage forms for oral administration contain, for example, 40 mg to 120 mg, more preferably 60 mg to 100 mg of iron.

Preferably, however, aqueous solutions are administered orally as in the form of drinkable formulations, such as syrup, elixir, solution, suspension or juice.

The medicaments according to the invention can optionally contain further constituents, such as conventional pharmaceutical carrier or auxiliary substances, such as binders or lubricants, diluents, disintegrating agents, fillers etc. Tablets can be coated with conventional film-forming agents. Aroma substances, flavourings and dyestuffs can furthermore be added, if desired.

The medicament according to the invention can optionally also contain further pharmacologically active constituents, which are chosen from the group consisting of vitamins, such as ascorbic acid, trace elements, mineral substances, nutrients and cofactors. The further pharmacologically active constituent(s) is/are preferably the vitamins (β-carotene, thiamine (vitamin $B_1$), riboflavin (vitamin $B_2$), pyridoxine (vitamin $B_6$), cyanocobalamin (vitamin $B_{12}$), cholecalciferol (vitamin $D_3$), α-tocopherol (vitamin E) and biotin (vitamin H), the cofactors pantothenic acid, nicotinamide and folic acid, the trace elements/minerals copper, manganese, zinc, calcium, phosphorus and/or magnesium and the nutrients amino acids, oligopeptides, carbohydrates and fats, optionally in the form of physiologically acceptable salts. Possible physiologically acceptable salts are all the conventional physiologically acceptable salts, preferably salts of inorganic acids or bases, such as hydrochlorides, sulfates, chlorides, phosphates, hydrogen phosphates, dihydrogen phosphates or hydroxides, or salts of organic acids, such as e.g. acetates, fumarates, maleates, citrates etc. The further pharmacologically active constituents can also be present as hydrates or solvates. Phosphorus is preferably added in the form of phosphates or hydrogen phosphates.

The "mixed valence compounds" according to the invention are stable and can release iron(II) or iron(III) to a physiological environment in a controlled manner. Without being limited to one theory, polynuclear iron hydroxide, to which the carbohydrates are bonded as a complex and/or via hydrogen bridge bonds, is present in the compounds according to the invention as a type of chemical matrix. In addition to iron(III), iron(II) is also present in the iron-carbohydrate complex compounds according to the invention, but surprisingly has a reduced toxicity in this form.

The majority of the iron hydroxide-carbohydrate complex compounds according to the invention have an $LD_{50}$ value of from about 200 mg of Fe/kg of body weight to 600 mg of Fe/kg of body weight. This $LD_{50}$ value is determined intravenously on mice. In comparison with this, for example, the $LD_{50}$ of Fe(II) sulfate is only 11 mg of Fe/kg of body weight, likewise determined intravenously on mice (Berenbaum et al. 1960 cited in P. Geisser, M. Baer, E. Schraub: Arzneimittelforschung Drug Research 42 (II), 12, 1439-1452 (1992).

The invention also provides the use of the iron(III)-iron(II)-carbohydrate complexes according to the invention for treatment and prophylaxis of iron deficiency anaemias and for the preparation of medicaments for treatment of iron deficiency anaemias. The medicaments are suitable for use in human and veterinary medicine.

The iron-carbohydrate complex compounds according to the invention are thus also suitable for the preparation of a medicament for treatment of patients suffering from symptoms of an iron deficiency anaemia, such as, for example: fatigue, lack of drive, lack of concentration, low cognitive efficiency, difficulties in finding the correct words, forgetfulness, unnatural paleness, irritability, acceleration in heart rate (tachycardia), sore or swollen tongue, enlarged spleen, craving in pregnancy (pica), headaches, loss of appetite, increased susceptibility to infection and depressive moods.

The iron-carbohydrate complex compounds according to the invention are furthermore suitable for the preparation of a medicament for treatment of iron deficiency anaemia in pregnant women, latent iron deficiency anaemia in children and young people, iron deficiency anaemia as a result of gastrointestinal abnormalities, iron deficiency anaemia as a result of blood losses, such as by gastrointestinal haemorrhages (e.g. as a result of ulcers, carcinomas, haemorrhoids, inflammatory disorders, intake of acetylsalicylic acid), menstruation or injuries, iron deficiency anaemia as a result of psilosis (sprue), iron deficiency anaemia as a result of reduced iron intake with the diet, in particular in selectively eating children and young people, immunodeficiency caused by iron deficiency anaemia, impairment of cerebral performance caused by iron deficiency anaemia and restless leg syndrome.

The iron-carbohydrate complex compounds used according to the invention are administered, in particular, orally or parenterally. The daily dose is, for example, between 10 and 500 mg of iron(III)/(II) per day of use. Patients with iron deficiency or iron deficiency anaemia take e.g. in each case 100 mg of iron(III)/(II) 2 to 3 times daily, and pregnant women take 60 mg of iron(III)/(II) 1 to 2 times daily (in each case calculated as iron (III)/(II), not as the complex).

The administration can take place without objection over a period of several months until the iron status has improved, reflected, for example, by the haemoglobin value, the transferrin saturation and the ferritin value of the patients, or until there is the desired improvement of a impairment in cerebral performance, immune response or symptoms of restless leg syndrome caused by iron deficiency anaemia.

The preparation according to the invention can be taken by children, adolescents and adults.

The use according to the invention proceeds, in particular, by means of improvement in the iron, haemoglobin, ferritin and transferrin values, which, in particular in young people and children, but also in adults, is accompanied by an improvement in the short-term memory test (STM), in the long-term memory test (LTM), in the Raven progressive matrices test, in the Wechsler adult intelligence scale (WAIS) and/or in the emotional coefficient (Baron EQ-i), YV test; youth version), or an improvement in the levels of neutrophiles, the levels of antibodies and/or lymphocyte function.

PREPARATION EXAMPLES

The results of Examples 1 to 4 are summarized in Table 1.
The percentage data relate to percentages by weight.

Example 1

300 g dextrin (DE value 33) are dissolved in 750 ml water at 60° C.

341 g 12% FeCl$_3$ and 444 g 30% NaOH are metered in at 60° C. and a constant pH of 11±0.5 in the course of 30 min. The reaction solution is heated up to 100° C. and kept at this temperature for 30 min. The reaction solution is cooled to 25° C. and the pH is adjusted from 7.9 to 8.0 with 20% HCl. The solution is centrifuged for 30 min at 7,000 rpm and then filtered over an AF-50 filter. The product is precipitated out by addition of 92% ethanol in a volume ratio of 1:2.4 (reaction solution:ethanol) and, after a settling time of 1 hour, is isolated. The oily crude product is mixed with 92% ethanol until a solid results (2×200 ml), which is filtered off and then dried for 16 hours at 50° C. under 125 mbar. 126 g of a black, amorphous powder are obtained.

Example 2

194 g dextrin (DE value 33) are dissolved in 387 ml water at 60° C.

176 g 12% FeCl$_3$ and 229 g 30% NaOH are metered in at 60° C. and a constant pH of 11±0.5 in the course of 30 min. The reaction solution is heated up to 100° C. and kept at this temperature for 30 min. The reaction solution is cooled to 25° C. and the pH is adjusted from 7.2 to 8.0 with 30% NaOH. The solution is filtered over an AF-50 filter. The product is precipitated out by addition of 92% ethanol in a volume ratio of 1:2.4 (reaction solution:ethanol) and, after a settling time of 1 hour, is isolated. The oily crude product is mixed with 92% ethanol until a solid results (4×200 ml), which is filtered off and then dried for 16 hours at 50° C. under 125 mbar. 75 g of a black, amorphous powder are obtained.

Example 3

300 g dextrin (DE value 11) are dissolved in 1,200 ml water at 60° C.

660 g 6.2% FeCl$_3$ and 440 g 30% NaOH are metered in at 60° C. and a constant pH of 11±0.5 in the course of 30 min. The reaction solution is heated up to 100° C. and kept at this temperature for 30 min. The reaction solution is cooled to 25° C. and the pH is adjusted from 9.4 to 8.0 with 20% HCl. The solution is centrifuged for 30 min at 7,000 rpm and then filtered over an AF-50 filter. 1,400 ml of the reaction solution are precipitated out by addition of 92% ethanol in a volume ratio of 1:2.4 (reaction solution:ethanol), and after a settling time of 1 hour, the precipitate is isolated. The oily crude product is mixed with 92% ethanol until a solid results (300 ml), which is filtered off and then dried for 16 hours at 50° C. under 125 mbar. 50 g of a black, amorphous powder are obtained.

Example 4

251 g maltose syrup (aqueous solution 80%—DE value 39) are dissolved in 1,200 ml water at 60° C. The pH of the solution is adjusted to 11.0 with 16 ml 30% NaOH. 600 g 6.2% FeCl$_3$ and 372 g 30% NaOH are metered in at 60° C. and a constant pH of 11±0.2 in the course of 60 min. The reaction solution is heated up to 100° C. and kept at this temperature for 30 min. The reaction solution is cooled to 25° C. and the pH is adjusted from 7.9 to 6.0 with 20% HCl. The solution is filtered over an AF-50 filter. Half of the reaction solution is precipitated out by addition of 92% ethanol in a volume ratio of 1:2.4 (reaction solution:ethanol) and, after a settling time of 1 hour, the crude product is isolated. The oily crude product is mixed with 92% ethanol until a solid results (300 ml), which is filtered off and then dried for 16 hours at 50° C. under 125 mbar. 37 g of a black, amorphous powder are obtained.

TABLE 1

| Parameter | Ex. 1 | Ex. 2 | Ex. 3 | Ex. 4 |
|---|---|---|---|---|
| Fe content (%) | 20.7 | 16.9 | 18.1 | 25.9 |
| Fe(III) content (%) | 15.5 | 11.7 | 16.7 | 22.1 |
| Fe(II) content (%) | 5.2 | 5.2 | 1.4 | 3.8 |
| Fe(III)/Fe(II) ratio | 75/25 | 69/31 | 92/8 | 85/15 |
| NaCl content (%) | 2.5 | 2.4 | 3.2 | 1.6 |
| Carbohydrate content[1] (%) | 57 | 63 | 63 | 53 |
| pH | 8.3 | 8.7 | 8.4 | 6.3 |
| $M_w$[2] | 16,000 | 18,000 | 43,000 | 16,000 |
| $M_n$[2] | 10,000 | 12,000 | 18,000 | 11,000 |
| P[3] | 1.6 | 1.5 | 2.5 | 1.4 |
| Fe yield (%) | 64 | 60 | 33 | 52 |

[1]Carbon content determined in accordance with ASTM D5291 and calculated for anhydroglucose
[2]Determined by GPC against pullulan as the standard
[3]P = Mw/Mn (polydispersity)

The invention claimed is:

1. An iron-carbohydrate complex compound comprising from 3 to 50 wt % of iron (II) based on the total amount of iron in the complex compound, and comprising 5 to 40 wt % iron based on the iron-carbohydrate complex compound, wherein a carbohydrate ligand of the iron-carbohydrate complex compound is selected from the group consisting of maltodextrins and maltose syrups having a dextrose equivalent of 3 to 50, partially hydrolyzed starch, and glucose syrups having a dextrose equivalent of more than 50.

2. The iron-carbohydrate complex compound of claim 1 comprising 10 to 80 wt % of one or more carbohydrates.

3. The iron-carbohydrate complex compound of claim 1 comprising
   (a) 5 to 40 wt. % of iron, of which 3 to 50 wt. %, based on the total amount of iron, is present in the form of iron(II),
   (b) 10 to 80 wt. % of one or more carbohydrates, and
   (c) sufficient oxygen and hydrogen in bonded form not including that in the carbohydrates and further optional elements to bring the total weight percent to 100%.

4. The iron-carbohydrate complex compound of claim 1, comprising
   (a) 10 to 30 wt. % of iron, of which 5 to 40 wt. %, based on the total amount of iron, is present in the form of iron(II),
   (b) 20 to 70 wt. % of one or more carbohydrates, and
   (c) sufficient oxygen and hydrogen in bonded form not including that in the carbohydrates and further optional elements to bring the total weight percent to 100%.

5. The iron-carbohydrate complex compound of claim 1 having a weight-average molecular weight of 10 to 80 kDa.

6. A process of preparing an iron-carbohydrate complex compound of claim 1, the process comprising:
   (a) preparing an aqueous solution or suspension of one or more carbohydrates selected from the group consisting of maltodextrins and maltose syrups having a dextrose equivalent of 3 to 50, partially hydrolyzed starch and glucose syrups having a dextrose equivalent of more than 50,
   (b) adding an iron(III) salt, at a constant pH in the range of 7-13,
   (c) heating the aqueous solution or suspension,
   (d) cooling the aqueous solution or suspension and
   (e) isolating the iron-carbohydrate complex compound formed.

7. The process of claim 6, further comprising, after step (d), step (d') of adjusting the pH of the aqueous solution or suspension to a value of between 5 and 9.

8. The process of claim 6, wherein the iron(III) salt is selected from the group consisting of iron(III) chloride and iron(III) sulfate and combinations thereof.

9. The process of claim 6, wherein step (c) comprises heating the aqueous solution or suspension at more than 80° C. for at least 30 min.

10. The process of claim 6, wherein the pH is kept constant in step (b) or step (c).

11. The process of claim 7, further comprising after (d'), step (d"): separating solids from the solution or suspension and wherein (e) comprises precipitating the iron-carbohydrate complex compound from the solution or suspension.

12. The process of claim 11, wherein step (d") is a procedure selected from the group consisting of filtration, centrifugation and combinations thereof.

13. The process of claim 11, wherein (e), precipitating the iron-carbohydrate complex compound from the solution or suspension includes contacting the solution or suspension with an alcohol.

14. The process of claim 13, wherein the alcohol is ethanol, and wherein, after (c), the process further comprises filtering the mixture to yield a solid, and vacuum drying the solid.

15. The iron-carbohydrate complex compound, obtained by the process of claim 6.

16. A medicament comprising the iron-carbohydrate complex compound of claim 1.

17. A method of treating iron deficiency anaemias comprising, administering to a patient the iron-carbohydrate complex compound of claim 1.

18. A medicament for treatment of iron deficiency anaemias the medicament comprising the iron-carbohydrate complex compound of claim 1.

19. A method of administering the iron-carbohydrate complex compound of claim 17 to a patient comprising oral or parenteral administration.

20. The method of claim 17, wherein the iron-carbohydrate complex compound is provided in a drinkable formulation, selected from the group consisting of syrup, elixir, solution, suspension, juice, and combinations thereof.

21. A method of treating patients suffering from symptoms of an iron deficiency anaemia, the method comprising administering to a patient the iron-carbohydrate complex compound of claim 15.

22. The method of claim 21, wherein the symptoms include:
fatigue, lack of drive, lack of concentration, low cognitive efficiency, difficulties in finding the correct words, forgetfulness, unnatural paleness, irritability, acceleration in heart rate (tachycardia), sore or swollen tongue, enlarged spleen, craving in pregnancy (pica), headaches, loss of appetite, increased susceptibility to infection and depressive moods.

23. The method of claim 21, wherein the cause or the symptom of the iron deficiency anaemia is selected from pregnancy, youth, gastrointestinal abnormalities, blood losses, gastrointestinal haemorrhages, ulcers, carcinomas, haemorrhoids, inflammatory disorders, intake of acetylsalicylic acid, menstruation, injuries, psilosis (sprue), reduced iron intake with the diet, immunodeficiency, impairment of cerebral performance, and restless leg syndrome.

* * * * *